(12) United States Patent
Crozet et al.

(10) Patent No.: US 12,077,493 B2
(45) Date of Patent: Sep. 3, 2024

(54) METHOD FOR PRODUCING ESTOLIDE ESTERS AND COMPOSITION OF ESTOLIDE ESTERS

(71) Applicants: TOTALENERGIES ONETECH, Courbevoie (FR); NYCO, Paris (FR)

(72) Inventors: Delphine Crozet, Villeurbanne (FR); Alice Limoges, Ternay (FR); Djibril Faye, Eragny (FR); Yves Travert, Eragny (FR); Grégoire Hervé, Paris (FR)

(73) Assignees: TOTALENERGIES ONETECH, Courbevoie (FR); NYCO, Paris (FR)

( * ) Notice: Subject to any disclaimer, the term of this patent is extended or adjusted under 35 U.S.C. 154(b) by 0 days.

(21) Appl. No.: 17/997,343

(22) PCT Filed: Apr. 27, 2021

(86) PCT No.: PCT/EP2021/061019
§ 371 (c)(1),
(2) Date: Oct. 27, 2022

(87) PCT Pub. No.: WO2021/219663
PCT Pub. Date: Nov. 4, 2021

(65) Prior Publication Data
US 2023/0219876 A1     Jul. 13, 2023

(30) Foreign Application Priority Data

Apr. 28, 2020 (FR) .................................... 2004219

(51) Int. Cl.
| | |
|---|---|
| *C07C 67/08* | (2006.01) |
| *A61K 8/37* | (2006.01) |
| *A61Q 19/00* | (2006.01) |
| *C10M 105/40* | (2006.01) |
| *C10M 105/42* | (2006.01) |

(52) U.S. Cl.
CPC ................ *C07C 67/08* (2013.01); *A61K 8/37* (2013.01); *A61Q 19/00* (2013.01); *C10M 105/40* (2013.01); *C10M 105/42* (2013.01); *A61K 2800/10* (2013.01); *C10M 2203/003* (2013.01); *C10M 2207/2885* (2013.01); *C10M 2207/301* (2013.01)

(58) Field of Classification Search
CPC .......... A61Q 19/00; A61K 8/37; A61K 8/375; A61K 2800/10; C10M 105/40; C10M 105/42; C10M 2207/2885; C10M 2207/301; C10M 2203/003; C07C 67/08; C07C 69/675; C07C 69/67
See application file for complete search history.

(56) References Cited

U.S. PATENT DOCUMENTS

2015/0094246 A1   4/2015  Bredsguard
2015/0247104 A1*  9/2015  Brekan .............. C10M 169/042
                                                508/496

FOREIGN PATENT DOCUMENTS

WO    WO-2008040864 A1 *  4/2008 ............. C07C 67/08

OTHER PUBLICATIONS

J. Salimon, "Chemically modified biolubricant basestocks from epoxidized oleic acid: Improved low temperature properties and oxidative stability," Journal of Saudi Chemical Society, Aug. 31, 2010, vol. 15, No. 3, pp. 195-201.

* cited by examiner

*Primary Examiner* — Vishal V Vasisth
(74) *Attorney, Agent, or Firm* — DUANE MORRIS LLP; Gregory M. Lefkowitz; Brandon A. Chan

(57) ABSTRACT

The invention relates to a method for the preparation of estolide esters from a hydroxycarboxylic acid by a reaction of addition of a fatty acid to the hydroxyl function and by a reaction of esterification of the carboxylic acid function with an alcohol. The invention further relates to the use of estolide esters as a base oil in a lubricating composition or as an emollient in a cosmetic or pharmaceutical composition.

15 Claims, No Drawings

METHOD FOR PRODUCING ESTOLIDE ESTERS AND COMPOSITION OF ESTOLIDE ESTERS

CROSS-REFERENCE TO RELATED APPLICATIONS

This application is a § 371 national stage entry of International Application No. PCT/EP2021/061019, filed on Apr. 27, 2021, which claims priority to French Patent Application No. FR2004219, filed on Apr. 28, 2020, the entire contents of which are incorporated herein by reference.

TECHNICAL FIELD OF THE INVENTION

A method for preparing a composition of estolide esters having an improved selectivity to ester monoestolides and a good conversion rate.

The invention further relates to a composition of estolide esters obtainable by the method according to the invention and to the use thereof as a base oil in a lubricating composition. The composition of estolide esters according to the invention can also be used in cosmetic or pharmaceutical compositions.

PRIOR ART

Lubricating compositions, also known as lubricants, are widely used for reducing friction between the surfaces of moving parts and thus reduce wear and prevent deterioration at the surface of said parts. The lubricants typically comprise a base oil and one or a plurality of functional additives.

When the lubricating composition is subject to high stresses (i.e. high pressures) during the use thereof, the lubricating compositions of which the base oil consists of hydrocarbons, tend to degrade and the parts are then damaged.

Lubricant manufacturers have to constantly improve the formulations thereof so as to meet increased fuel economy requirements while maintaining engine cleanliness and reducing emissions. Such requirements force manufacturers to examine the formulation capabilities thereof and/or to search for new base oils which can meet performance requirements.

To produce lubricants, such as engine oils, transmission fluids, gear oils, industrial lubricating oils, oils for metalwork, etc., one typically starts with an oil of lubricating grade from a refinery, or a suitable polymerized petrochemical fluid. In such base oil, additives are mixed for improving the properties and performance thereof, such as increased lubricity, anti-wear and anti-corrosion properties, and resistance of the lubricant to heat and/or oxidation. In this way, various additives such as antioxidants, corrosion inhibitors, dispersants, defoamers, metal deactivators and other additives which can be used in lubricant formulations, can be added in conventional effective amounts.

Environmental concerns and restrictions lead manufacturers to find alternatives to sources of petroleum (fossil) origin. Oils of plant or animal origin have thus proved to be interesting sources of base oils. In particular, the oils of plant or animal origin can be converted into acids or esters by conventional methods.

In the API classification of base oils, esters are referred to as Group V base oils Synthetic esters can be used in both as a base oil and as an additive in lubricants. In comparison with cheaper but less environmentally safe mineral oils, synthetic esters were mainly used as base oils whenever the viscosity/temperature behavior had to meet strict requirements. The increasingly important issues of environmental acceptability and biodegradability underly the desire to find alternatives to mineral oil as a raw material in lubrication applications.

The cosmetics, dermatology and pharmacy markets are increasingly demanding ingredients of biological origin for the formulation of the products thereof. While bio-sourced active ingredients, emulsifiers and vegetable oils have been strongly developed in recent years and are now widely available on the market, emollients of 100% organic origin are still rare.

The emollients currently used in cosmetics are either isoparaffins coming from petrochemistry (mainly isododecane and isohexadecane), white oils, silicone oils or ester oils (either synthetic or natural). Isoparaffins, white oils and silicone oils are widely distributed because same are very stable and odorless, but do not come from a renewable resource. Although volatile silicones such as cyclomethicone have long been considered as emollients and solvents which are harmless to the skin (International Journal of Toxicology, Vol. 10, no. 1, pp. 9-19, 1991), concerns have been expressed in recent years regarding the potential harmful effects thereof on the environment and even on human health (in particular with regard to octamethylcyclotetrasiloxane).

Environmental concerns and restrictions lead manufacturers to find alternatives to sources of petroleum (fossil) origin. Oils of plant or animal origin have thus proved to be interesting sources of base oils or emollients. In particular, the oils of plant or animal origin can be converted into acids or esters by conventional methods. Such acids can then be converted into unsaturated alcohols, e.g. from triglyceride oil, by one or a plurality of steps of hydrogenation of fatty acids or methyl esters.

Estolides are biodegradable base oils of biological origin which can be used in lubricants.

The document U.S. Pat. No. 2015/0094246 describes compositions of estolides intended for being used in lubricating compositions. Said document describes a preparation method wherein fatty acids such as oleic acids are reacted in the presence of a catalyst, such reaction step being followed by a Myers 15 centrifugal distillation step, at 200 or 300° C. under an absolute pressure of 12 microns (0.012 torr) in order to remove the monoestolides.

S. C. Cermak et al., J. Am. Oil Chem. Soc. (2013) 90:1895-1902, described the preparation of estolides from a composition of unsaturated fatty acids comprising 90% oleic acids and butyric or acetic acid. Said document discloses a step of separation by vacuum distillation of the monoestolides from the polyestolides.

A plurality of reactions competes when unsaturated fatty acids or unsaturated fatty acid esters are made to react with saturated acids in the presence of a catalyst. In this way, the intended reaction for forming the estolides is a reaction of addition of the acid function to a carbon-carbon double bond. Transesterification reactions can also occur however. The reaction between the unsaturated acid or the ester thereof with the unsaturated fatty acid can also lead to polyestolides.

The methods described in the prior art cannot be used for obtaining a satisfactory selectivity to the monoestolide ester while keeping a good degree of conversion.

The applicant has found, surprisingly, that it was possible to obtain a composition of estolides with a high selectivity to monoestolides, along with a satisfactory conversion.

SUMMARY OF THE INVENTION

The invention relates to a preparation method for a composition C5 of estolide esters, said method comprising:

a) provision of a composition C1 comprising at least one hydroxycarboxylic acid containing from 10 to 30 carbon atoms, b) followed by:

b1) the introduction of a composition C2 comprising at least one saturated acid containing 2 to 18 carbon atoms, into the composition C1 in order to obtain a composition C3 of acid estolides, the hydroxycarboxylic acid/saturated fatty acid molar ratio being at least 1/2, then the introduction of a composition C4 comprising at least one saturated alcohol containing 1 to 16 carbon atoms, into the composition C3, or b2) the introduction of a composition C4 comprising at least one saturated alcohol containing 1 to 16 carbon atoms, into composition C1 in order to obtain a composition C6 of hydroxycarboxylic acid ester, followed by the introduction of a composition C2 comprising at least one saturated acid containing from 2 to 18 carbon atoms, into the composition C6, the molar ratio of hydroxycarboxylic acid ester to saturated fatty acid being at least 1/1.3, (c) Obtaining a composition C5 of estolide esters.

According to one embodiment of the invention, the hydroxycarboxylic acid/saturated fatty acid molar ratio ranges from 1/2 to 1/8, preferentially from 1/2 to 1/6 when the method is carried out according to the route b1) and the hydroxycarboxylic acid ester/saturated fatty acid molar ratio ranges from 1/1.4 to 1/6, preferentially from 1/1.4 to 1/4 when the method is carried out according to the route b2).

According to one embodiment of the invention, the hydroxycarboxylic acid corresponds to the formula (1), the saturated fatty acid corresponds to the formula (2) and the saturated alcohol corresponds to the formula (4):

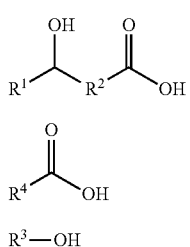

[Chem 1]

[Chem 2]

[Chem 4]

wherein:

$R^1$ represents a linear or branched alkyl radical comprising from 1 to 27 carbon atoms, preferentially from 3 to 18 carbon atoms, more preferably from 5 to 12 carbon atoms, $R^2$ represents a linear or branched divalent alkylene radical comprising from 1 to 27 carbon atoms, preferentially from 4 to 22 carbon atoms, more preferably from 8 to 18 carbon atoms, where it is understood that the total number of carbon atoms of R1 and R2 ranges from 8 to 28, preferentially from 6 to 24, more preferably from 10 to 20 carbon atoms, $R^3$ represents a linear or branched monovalent alkyl radical containing from 1 to 16 carbon atoms, preferentially from 1 to 12 carbon atoms, advantageously from 1 to 10 carbon atoms, $R^4$ represents a linear or branched monovalent alkyl radical containing from 1 to 17 carbon atoms, preferentially a linear or branched alkyl containing from 2 to 12 carbon atoms, advantageously a linear alkyl containing from 4 to 12 carbon atoms.

According to one embodiment of the invention, the C5 composition of estolide esters comprises monoestolides with the formula (7):

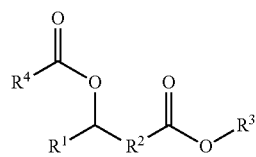

[Chem 7]

wherein $R^1$, $R^2$, $R^3$ and $R^4$ have the same definition as given above.

According to one embodiment of the invention, the catalyst for the fatty acid addition reaction is used in a proportion ranging from 0.01 to 0.1% by weight, preferentially from 0.02 to 0.08% by weight, with respect to the total weight of the reaction medium.

According to one embodiment of the invention, the method comprises:

b1) the reaction of said saturated acid with the hydroxyl function of said hydroxycarboxylic acid at a temperature ranging from 120 to 280° C., for obtaining acid estolides, followed by the reaction of said saturated alcohol with the acid function of the acid estolides at a temperature ranging from 120 to 280° C., for obtaining a composition C5 of estolide esters, or b2) the reaction of said saturated alcohol with the acid function of the hydroxycarboxylic acid ester at a temperature ranging from 120 to 280° C., for obtaining the esters of the hydroxycarboxylic acid and of the alcohol, followed by the reaction of said saturated acid on the hydroxyl function of the esters of the hydroxycarboxylic acid and of the alcohol at a temperature ranging from 120 to 280° C., for obtaining a composition C5 of estolide esters.

According to one embodiment of the invention, the method is carried out according to the route b1).

The present invention further relates to a composition of estolide esters which can be obtained by the method according to the invention, comprising, with respect to the total weight of the estolides:

more than 50% to 99.9% by weight of monoestolide ester(s) with the formula (7), and from 0.1 to less than 50% by weight of polyestolide ester(s) with the formula (8), with

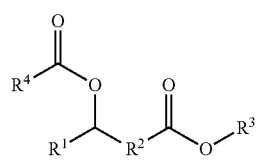

[Chem 7]

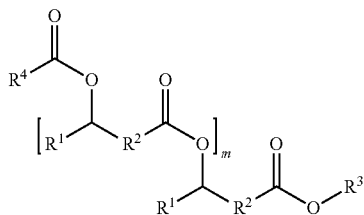

[Chem 8]

wherein:

$R^1$ represents a linear or branched alkyl radical comprising from 1 to 27 carbon atoms, preferentially from 3 to 18 carbon atoms, more preferentially from 5 to 12 carbon atoms, $R^2$ represents a linear or branched divalent alkylene radical comprising from 1 to 27 carbon atoms, preferentially from 4 to 22 carbon atoms, more preferentially from 8 to 18 carbon atoms, where it is understood that the total number of carbon atoms of R1 and R2 ranges from 8 to 28, preferentially from 6 to 24, more preferentially from 10 to 20 carbon atoms, $R^3$ represents a linear or branched monovalent alkyl radical containing from 1 to 16 carbon atoms, preferentially from 1 to 12 carbon atoms, advantageously from 1 to 10 carbon atoms, $R^4$ represents a linear or branched monovalent alkyl radical containing from 1 to 17 carbon atoms, preferentially a linear or branched alkyl containing from 2 to 12 carbon atoms, advantageously a linear alkyl containing from 4 to 12 carbon atoms, and m is a number different from zero, typically ranging from 1 to 4.

The invention further relates to the use of the composition of estolide esters according to the invention, as a base oil in a lubricating composition or as an emollient in a cosmetic or pharmaceutical composition.

Finally, the invention relates to a lubricating composition comprising the composition of estolide esters according to the invention and at least one base oil different from the estolide esters and/or at least one additive different from the estolide esters.

The method according to the invention makes it possible to obtain a good selectivity to the formation of monoestolides. In addition to the good selectivity to monoestolides, the method according to the invention can be used for obtaining polyestolides with a low number of addition reactions. In other words, at least 50% by weight, or even at least 70% by weight, or even at least 90% by weight of the polyestolides which will be obtained in the method according to the invention will be polyestolides where EN (estolide number) is equal to 2, and it is understood that, as defined in the present invention, that EN is equal to 1 for the monoestolides and EN is strictly greater than 1 for the polyestolides.

The method according to the invention makes it possible to skip the step of separating the monoestolides from the polyestolides, a step which can be sometimes difficult to implement.

DETAILED DESCRIPTION OF THE INVENTION

The invention relates to a preparation method for a composition C5 of estolide esters, said method comprising:

a) The provision of a composition C1 comprising at least one hydroxycarboxylic acid containing from 10 to 30 carbon atoms,
b) Followed by:
   b1) the introduction of a composition C2 comprising at least one saturated acid containing 2 to 18 carbon atoms, into the composition C1 in order to obtain a composition C3 of acid estolides, the hydroxycarboxylic acid/saturated fatty acid molar ratio being at least 1/2, followed by the introduction of a composition C4 comprising at least one saturated alcohol containing 1 to 16 carbon atoms, into the composition C3, or
   b2) the introduction of a composition C4 comprising at least one saturated alcohol containing 1 to 16 carbon atoms, into composition C1 in order to obtain a composition C6 of hydroxycarboxylic acid ester, followed by the introduction of a composition C2 comprising at least one saturated acid containing from 2 to 18 carbon atoms, into the composition C6, the molar ratio of hydroxycarboxylic acid ester to saturated fatty acid being at least 1/1.3,
c) Preparing a composition C5 of estolide esters.

Thereby, the method according to the invention typically comprises:
the reaction of the acid function of at least one saturated acid containing from 2 to 18 carbon atoms with the hydroxyl function of at least one hydroxycarboxylic acid containing from 10 to 30 carbon atoms or the ester of said hydroxycarboxylic acid, and
the reaction of the alcohol function of at least one saturated alcohol containing 1 to 16 carbon atoms with the acid function of at least one hydroxycarboxylic acid or of the acid estolide resulting from said hydroxycarboxylic acid,
it is understood that the reaction of the saturated fatty acid can be carried out before (embodiment according to b1) or after the reaction of the saturated alcohol with the hydroxycarboxylic acid (embodiment according to b2).

As defined in the present invention, an "estolide" refers to the product resulting from the reaction of addition of a carboxylic acid function of a saturated fatty acid with the hydroxyl function of a hydroxycarboxylic acid. The term "estolide" in the present invention will refer both to a "monoestolide" and to a "polyestolide".

As defined by the present invention, a "monoestolide" refers to an estolide resulting from a single addition reaction between a hydroxyl function of a hydroxycarboxylic acid with an acid function of a saturated fatty acid. The monoestolide can be in acid form or in ester form. The monoestolide in acid form is then esterified in order to obtain a monoestolide ester falling within the scope of the present invention.

As defined by the present invention, a "polyestolide" refers to the product resulting from the reaction between at least two hydroxycarboxylic acid compounds, followed, if appropriate, by the reaction with a saturated fatty acid. The polyestolide can be in acid form or in ester form depending on the acid or ester form of the unsaturated compound. The polyestolide in acid form is then esterified in order to obtain a polyestolide ester falling within the scope of the present invention.

Preferentially, the method according to the invention does not include a vacuum distillation step for separating the monoestolides produced from the polyestolides produced. In particular, the method according to the invention does not comprise Myers vacuum distillation for separating monoestolides from polyestolides.

Indeed, the method according to the invention has a high selectivity in favor of monoestolides, which makes it possible to skip such a distillation step.

It should be noted that the method according to the invention can comprise one or a plurality of operations for separating the saturated acid and/or the saturated alcohol and/or the hydroxycarboxylic acid, the starting reagent of the method according to the invention, or the intermediate hydroxycarboxylic acid monoester, from the composition C5 of estolide esters obtained at the completion of the method. Such operations can be steps of evaporation by stripping or distillation operations, where it is understood that such distillation operations are distinct from the distillation steps separating the monoestolides from the polyestolides.

The method according to the invention can further comprise one or a plurality of washing operations for separating the homogeneous catalyst from the product resulting from the method according to the invention or one or a plurality of filtration steps for separating the heterogeneous catalyst from the product resulting from the method according to the invention.

As a preliminary matter, it should be noted that, in the following description and claims, the expression "comprised between" has to be understood as including the limits mentioned.

Composition C1 of hydroxycarboxylic acids

The method according to the invention uses at least one hydroxycarboxylic acid as reagent for the reaction with the saturated fatty acid or with the saturated alcohol.

As defined by the present invention, the hydroxycarboxylic acid comprises at least one carboxylic acid function (—COOH) and at least one hydroxyl function (—OH). Preferentially, the hydroxycarboxylic acid comprises a single carboxylic acid function and a single hydroxyl function. More preferentially, the hydroxycarboxylic acid is a saturated acid which typically does not comprise any function other than the carboxylic acid function and the hydroxyl function.

According to a preferred embodiment, the hydroxycarboxylic acid comprises a linear or branched, preferentially linear, alkyl chain.

The hydroxycarboxylic acid used in the invention comprises from 10 to 30 carbon atoms, preferentially from 12 to 24 carbon atoms, more preferentially from 14 to 20 carbon atoms.

According to a preferred embodiment, the hydroxycarboxylic acid used in the invention comprises at least one hydroxyl functional group carried by a secondary carbon atom (a so-called secondary alcohol compound).

According to one embodiment, the hydroxycarboxylic acid used in the invention comprises at least one carboxylic acid function carried by a secondary carbon atom.

Preferentially, the hydroxycarboxylic acid has the formula (1):

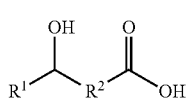

[Chem 1]

Wherein:
$R^1$ represents a linear or branched alkyl radical comprising from 1 to 27 carbon atoms, preferentially from 3 to 18 carbon atoms, more preferentially from 5 to 12 carbon atoms, $R^2$ represents a linear or branched divalent alkylene radical comprising from 1 to 27 carbon atoms, preferentially from 4 to 22 carbon atoms, more preferentially from 8 to 18 carbon atoms, where it is understood that the total number of carbon atoms of $R^1$ and $R^2$ ranges from 8 to 28, preferentially from 6 to 24 carbon atoms, more preferentially from 10 to 20 carbon atoms.

Preferentially, in the formula (1):
$R^1$ represents a linear alkyl radical comprising from 3 to 18 carbon atoms, preferentially from 5 to 12 carbon atoms,
$R^2$ represents a linear alkylene divalent radical comprising from 4 to 22 carbon atoms, preferentially from 8 to 18 carbon atoms,
where it is understood that the total number of carbon atoms of $R^1$ and $R^2$ ranges from 6 to 24 carbon atoms, preferentially from 10 to 20 carbon atoms.

Preferentially, the hydroxycarboxylic acid used in the invention is 12-hydroxystearic acid.

Typically, the composition C1 used in the invention comprises at least 50% by weight of hydroxycarboxylic acid(s), preferentially at least 70% by weight, more preferentially at least 75% by weight, or even at least 80% by weight of hydroxycarboxylic acid(s), with respect to the total weight of the composition C1.

Preferentially, the composition C1 used in the invention comprises at least 50% by weight of hydroxycarboxylic acid(s), preferentially at least 70% by weight, more preferentially at least 90% by weight, or even at least 95% by weight of 12-hydroxystearic acid, with respect to the total weight of the composition C1.

The composition C1 can be commercially available.

Composition C2 of saturated acids

The method according to the invention uses as a reagent at least one saturated acid containing from 2 to 18 carbon atoms, preferentially a saturated fatty acid containing from 5 to 18 carbon atoms, for reacting on the alcohol function:
of the hydroxycarboxylic acid (of the composition C1) or
of the ester of the hydroxycarboxylic acid and of the saturated alcohol (composition C6).

Preferentially, the saturated acid is a saturated monoacid.

According to one embodiment, the saturated acid corresponds to the formula (2):

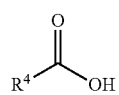

[Chem 2]

wherein $R^4$ represents a monovalent linear or branched alkyl radical containing from 1 to 17 carbon atoms, preferentially a linear or branched alkyl containing from 4 to 12 carbon atoms, advantageously a linear alkyl containing from 5 to 12 carbon atoms.

The saturated acid can be a linear or branched, preferentially linear acid.

Preferentially, the saturated acid is a saturated fatty acid and contains from 5 to 12 carbon atoms. Such chain length makes it possible to further optimize the cold properties of the composition of estolides resulting from the method.

According to one embodiment, the saturated fatty acid used in the invention is chosen from pentanoic acid, hexanoic acid, heptanoic acid, octanoic acid, nonanoic acid, decanoic acid, undecanoic acid, lauric acid and the mixture thereof.

The method according to the invention can use a single saturated fatty acid or a mixture of a plurality of saturated fatty acids. Preferentially, the method according to the invention uses a single saturated fatty acid.

It is also possible to envisage using a mixture of at least two different saturated fatty acids. The proportions can be adjusted according to the properties desired for the composition of estolides.

The composition C2 typically comprises at least 70% by weight of saturated fatty acid(s), preferentially at least 90% by weight, more preferentially at least 95% by weight, or even at least 98% by weight of saturated fatty acid(s), with respect to the total weight of the composition C2.

Preferentially, the composition C2 used in the invention comprises at least 70% by weight of the same saturated fatty acid, preferentially at least 90% by weight, more preferentially at least 95% by weight, or even at least 98% by weight of the same saturated fatty acid, with respect to the total weight of the composition C2.

The composition C2 can be commercially available and can be of either of natural or synthetic origin, preferentially of natural origin.

Composition C3 of acid estolides

The reaction of the hydroxyl function of the hydroxycarboxylic acid with the acid function of the saturated fatty acid leads to acid estolides.

Preferentially, the reaction uses a molar excess of saturated fatty acid for carrying out the reaction of the hydroxyl function of the hydroxycarboxylic acid and of the acid function of the saturated fatty acid. According to one embodiment, the hydroxycarboxylic acid/saturated fatty acid molar ratio ranges from 1/1.5 to 1/6, preferentially from 1/2 to 1/4.

If the hydroxycarboxylic acid is described by the formula (1) and the saturated fatty acid is described by the formula (2), then the acid estolide will be described by the formula (3):

[Chem 3]

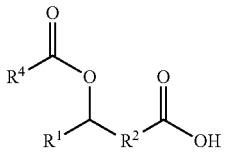

wherein $R^1$, $R^2$ and $R^4$ have the same meaning as in the formulae (1) and (2).

Composition C4 of saturated alcohol

The method according to the invention uses at least one saturated alcohol containing from 1 to 16 carbon atoms, as reagent in order to react on the acid function:
of the hydroxycarboxylic acid (of the composition C1) or
of the acid estolide (of the composition C3).

Preferentially, the alcohol corresponds to the formula (4):

$$R^3\text{—OH} \quad \text{[Chem 4]}$$

wherein R3 represents a linear or branched monovalent alkyl radical containing from 1 to 16 carbon atoms, preferentially from 1 to 12 carbon atoms, advantageously from 1 to 10 carbon atoms.

According to one embodiment, the alcohol is a primary or secondary alcohol containing from 1 to 16 carbon atoms, preferentially from 1 to 12 carbon atoms, advantageously from 1 to 10 carbon atoms.

According to one embodiment, the saturated alcohol used in the invention is chosen from methanol, ethanol, propanol, isopropanol, 1-butanol, 3-methylbutanol and hexanol, 1-octanol, 2-octanol, 2-ethylhexanol, 2-methylhexanol, 1-decanol, 2-methylbutanol, 1-nonanol, 1-heptanol, and mixtures thereof.

The method according to the invention can use a single saturated alcohol or a mixture of several saturated alcohols. Preferentially, the method according to the invention uses a single saturated alcohol.

Using a mixture of at least two different saturated alcohols, can be envisaged as well. The proportions can be adjusted depending on the properties desired for the composition of estolide esters.

The composition C4 typically comprises at least 70% by weight of saturated alcohol(s), preferentially at least 90% by weight, more preferentially at least 95% by weight, or even at least 98% by weight of saturated alcohol(s), with respect to the total weight of the composition C4.

Preferentially, the composition C4 used in the invention comprises at least 70% by weight of the same saturated alcohol, preferentially at least 90% by weight, more preferentially at least 95% by weight, or even at least 98% by weight of the same saturated alcohol, with respect to the total weight of the composition C4.

The composition C4 can be commercially available and can be of either of natural or synthetic origin, preferentially of natural origin.

Composition C6 of hydroxycarboxylic acid esters and alcohol esters

The reaction of the acid function of the hydroxycarboxylic acid with the alcohol function of the saturated alcohol leads to esters of the hydroxycarboxylic acid and of the alcohol.

According to one embodiment, the hydroxycarboxylic acid/saturated alcohol molar ratio ranges from 1/6 to 1/1, preferentially from 1/2 to 1/1.1.

If the hydroxycarboxylic acid is described by the formula (1) and the saturated alcohol is described by the formula (3), then the hydroxycarboxylic acid ester will be described by the formula (6):

[Chem 6]

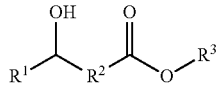

wherein $R^1$, $R^2$ and $R^3$ have the same meaning as in the formulae (1) and (3).

Implementation of the method according to the invention

The method according to the invention involves two chemical reactions:
a reaction of the saturated alcohol, and
a reaction of the saturated acid.

The two chemical reactions involved in the method according to the invention are typically carried out in the presence of a catalyst. The catalyst can be identical or different for each of the two reactions. The catalyst will preferentially be identical for both reactions.

The catalyst can be chosen from catalysts containing a Lewis acid, e.g. tin, titanate or boron trifluoride.

As an example, the catalyst can be paratoluenesulfonic acid (p-TSA), methanesulfonic acid (MSA), sulfuric acid, boron trifluoride etherate ($BF_3 \cdot EtO$), tin tetrachloride (FASCAT 4400 4100), tin dichloride (FASCAT 2004 256), dibutyltin dichloride (FASCAT 4210), monobutyltin oxide (FASCAT 4100, TIB KAT 256),) dibutyltin oxide (FASCAT 4201, TIB KAT 248), dioctyltin oxide (FASCAT 8201, TIB KAT 232), monobutyltin tris(2-ethylhexanoate (FASCAT 4102) tin oxalate (FASCAT 2001, TIB KAT 160), dibutyltin diacetate (FASCAT 4200, TIB KAT 233), dioctyltin diacetate (TIB KAT 223) and dioctyltin dicarboxylate (TIB KAT 318)).

According to one embodiment, the step b) of the method according to the invention comprises:
b1) the reaction of at least one saturated acid on the hydroxyl function of the hydroxycarboxylic acid at a temperature ranging from 120 to 280° C., for obtaining acid estolides, followed by the reaction of the saturated alcohol on the acid function of the acid estolides at a temperature ranging from 120 to 280° C., for obtaining a composition C5 of estolide esters,
or
b2) the reaction of the saturated alcohol with the acid function of the hydroxycarboxylic acid esters at a temperature of 120 to 280° C., for obtaining esters of the hydroxycarboxylic acid esters and of the alcohol, followed by the reaction of at least one saturated acid on the hydroxyl function of the esters of the hydroxycarboxylic acid and of the alcohol at a temperature ranging from 120 to 280° C., for obtaining a composition C5 of estolide esters.

According to a preferred embodiment, the step b) is carried out according to the route b1). Indeed, the inventors have discovered that the route b1) can be used for reducing transesterification reactions and for obtaining a lower acid number for the composition C5 of estolide esters.

The method according to the invention can be used in particular for obtaining, at the completion of the two reactions, a composition of estolide esters comprising predominantly ester monoestolides, in particular, the composition of estolide esters obtained at the completion of the method according to the invention typically comprises at least 50% by weight, advantageously at least 60% by weight of ester monoestolides, with respect to the total weight of the composition resulting from the method.

Unlike the production methods for estolides involving unsaturated compounds, as described in document U.S. Pat. No. 2015/0094246, the method according to the invention will not lead to a mixture of positional isomers depending on the position of the addition of the saturated fatty acid on the carbon-carbon double bond of the unsaturated compound. Indeed, in the prior art, the saturated fatty acid can react on one or other of the carbon atoms of the carbon-carbon double bond of the unsaturated compound, which then leads to two positional monoestolide isomers. Furthermore, part of the unsaturated compounds can be isomerized, so that the carbon-carbon double bond can change position for a portion of the unsaturated compounds. Indeed, in the prior art, the saturated fatty acid can react on one or the other of the carbon atoms of the carbon-carbon double bond of the unsaturated compound, which then leads to two isomers. Moreover, under the reaction conditions, said double bond can migrate along the alkyl chain, leading to a large number of isomers differing in the position of functionalization and the possible formation of lactones.

Contrary to such methods of the prior art, the method according to the invention leads to a composition of estolides free of positional isomers, insofar as the addition reaction of the saturated fatty acid is carried out selectively only in the position fixed by the hydroxyl function of the hydroxycarboxylic acid.

The ester monoestolides which can be obtained at the completion of the method can be represented by the formula (7):

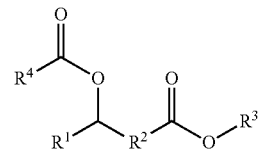

wherein:
$R^1$, $R^2$, $R^3$ and $R^4$ have the same definitions as in the formulae (1), (2) and (3), Preferentially, the method according to the invention does not comprise any subsequent step of hydrogenation of the composition of estolides obtained at the completion of the method.

"Composition resulting from the method" should refer to the reactants, the products and the by-products of the reaction. The catalyst is not taken into account when naming the composition resulting from the method. Thus, it will generally be appropriate to separate the catalyst from the reaction medium in order to obtain the composition of estolides resulting from the method.

The method can be carried out continuously or semi-continuously or in batches.

According to one embodiment, the method according to the invention uses a batch addition of the hydroxycarboxylic acid and the saturated fatty acid (simultaneous addition of all the reagents) or a fractionated addition (addition of a reagent in a fractionated, or progressive or continuous manner).

According to one embodiment according to the route b1), the reaction of the hydroxycarboxylic acid with the saturated fatty acid in the presence of the catalyst is carried out according to one or a plurality of the following conditions:
the molar ratio of hydroxycarboxylic acid to saturated fatty acid ranges from 1/2 to 1/8, preferentially from 1/2 to 1/6;
the catalyst for the fatty acid addition reaction is used in a proportion ranging from 0.01 to 0.1% by weight, preferentially from 0.02 to 0.08% by weight, with respect to the total weight of the reaction medium.

According to one embodiment according to the route b2), the reaction of the hydroxycarboxylic acid ester with the saturated fatty acid in the presence of the catalyst is carried out according to one or a plurality of the following conditions:
the molar ratio of hydroxycarboxylic acid ester to saturated fatty acid ranges from 1/1.3 to 1/6, preferentially from 1/1.4 to 1/4;
the catalyst for the fatty acid addition reaction is used in a proportion ranging from 0.01 to 0.1% by weight, preferentially from 0.02 to 0.08% by weight, with respect to the total weight of the reaction medium.

The progress of the reaction can be monitored by gas chromatography coupled to a flame ionization detector (GC-FID), according to methods known to a person skilled in the art.

As defined by the present invention, conversion refers to the amount by weight of hydroxycarboxylic acid which has reacted and selectivity refers to the amount by weight of monoestolides formed with respect to the total weight of the products formed (the calculation of selectivity thus does not take into account the reactants or the catalyst).

The composition of estolides obtained at the completion of the method can further comprise by-products (also called "secondary products"), e.g. polyestolides with the formula (8).

According to one embodiment, the method according to the invention can be used for obtaining polyestolides with the formula (8).

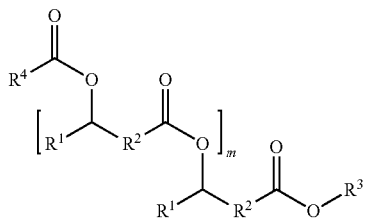

[Chem 8]

Wherein:
$R^1$, $R^2$, $R^3$ and $R^4$ have the same definitions as in the formulae (1), (2) and (4),
m is a number other than zero, typically m can range from 1 to 4.

In addition to the very good selectivity to monoestolides, the method according to the invention can be used for obtaining polyestolides with a low number of addition reactions. In other words, at least 50% by weight, or even at least 70% by weight, or even at least 90% by weight of the polyestolides which can be obtained in the method according to the invention will be polyestolides where m is equal to 1.

The composition of estolides obtained at the completion of the method advantageously has a kinematic viscosity at 40° C. ranging from 5 to 100 mm²/s, preferentially from 10 to 50 mm²/s, advantageously from 15 to 40 mm²/s, measured according to the standard ASTM D445.

The composition of estolides obtained at the completion of the method advantageously has an acid number less than or equal to 15 mgKOH/g, preferentially less than or equal to 5 mgKOH/g, even more preferentially less than or equal to 3 mgKOH/g. The acid number can be determined according to the standard ASTM D974.

The composition of estolides obtained at the completion of the reaction of formation of estolides (reaction of addition of saturated fatty acids to hydroxycarboxylic acid or hydroxycarboxylic acid ester) typically comprises:
more than 50% by weight to 99.9% by weight of monoestolide(s), and
0.1 to less than 50% by weight of polyestolide(s),
with respect to the total weight of the estolides, the estolides including monoestolides and polyestolides.

It should be noted that the composition of estolides can possibly comprise from 0.1 to 30% by weight of unreacted reactants or hydroxycarboxylic acid esters possibly formed in situ, with respect to the total weight of the composition of estolides.

Transesterification reactions can occur, in particular when the method is carried out according to the route b2). Indeed, when the saturated fatty acid(s) are reacted with the hydroxycarboxylic acid esters (the route b2), transesterification reactions can occur to form by-products. When the hydroxycarboxylic acid is described by the formula (1), the saturated fatty acid is described by the formula (2) and the fatty alcohol is described by the formula (4), then the by-products can be described by the formulae (5) and (3):

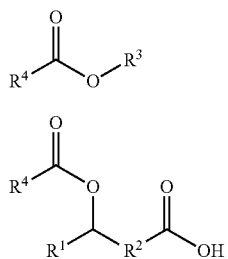

[Chem 5]

[Chem 3]

wherein $R^1$, $R^2$, $R^3$ and $R^4$ have the same definition as in the formulae (1), (2) and (4).

It should be noted that according to the route b2), the by-product with the formula (3) can be formed during the second esterification reaction, whereas same would be the target intermediate product according to the route b1).

The method according to the invention can possibly further comprise, after the reaction for the formation of the estolides, a separation step wherein the reagents which have not reacted such as a saturated fatty acid, a hydroxycarboxylic acid and/or a hydroxycarboxylic acid ester, are removed from the composition of estolides. As defined by the present invention, the estolides are not reagents.

Composition of Estolides

The subject matter of present invention further relates to a composition of estolide esters as such and a composition of estolides which can be obtained by the method according to the invention.

The composition of estolide esters according to the invention typically comprises:
more than 50% by weight to 99.9% by weight, preferentially from 55 to 99% by weight, more preferentially from 60 to 98% by weight, of monoestolide(s), and
from 0.1 to less than 50% by weight, preferentially from 1 to 45% by weight, more preferentially from 2 to 40% by weight, of polyestolide(s),
with respect to the total weight of the estolides, the estolides including monoestolides and polyestolides.

The composition of estolides according to the invention advantageously has a kinematic viscosity at 40° C. ranging from 5 to 100 mm²/s, preferentially from 10 to 50 mm²/s, advantageously from 15 to 40 mm²/s, measured according to the standard ASTM D445.

The composition of estolides according to the invention advantageously has an iodine value less than or equal to 13 g/100 g of iodine, preferentially less than or equal to 10 g/100 g of iodine, advantageously less than or equal to 8 g/100 g of iodine. The iodine value can be determined according to the standard ASTM D974.

The composition of estolides according to the invention advantageously has an acid number less than or equal to 15 mgKOH/g, preferentially less than or equal to 5 mgKOH/g, even more preferentially less than or equal to 3 mgKOH/g. The acid number can be determined according to the standard ASTM D974.

According to one embodiment, typically when the method is carried out according to the route b2), the composition of estolide esters comprises:
from 50 to 99.8% by weight, preferentially from 55 to 90% by weight, more preferentially from 55 to 80% by weight, of monoestolide(s),
from 0.1 to 30% by weight, preferentially from 5 to 25% by weight, more preferentially from 10 to 25% by weight, of polyestolide(s), and from 0.1 to 30% by weight, preferentially from 1 to 25% by weight, more preferentially from 5 to 25% by weight, of ester(s) chosen from hydroxycarboxylic acid esters, saturated fatty acid esters and saturated fatty alcohol esters, and mixtures thereof with respect to the total weight of the composition of estolides.

According to one embodiment of the invention, typically when the method is carried out according to the route b1), the composition of estolides comprises:

from 55 to 99.9% by weight, preferentially from 60 to 95% by weight, more preferentially from 65 to 90% by weight, of monoestolides corresponding to the formula (7), and from 0.1 to 45% by weight, preferentially from 5 to 40% by weight, more preferentially from 10 to 35% by weight, of polyestolides corresponding to the formula (8), with respect to the total weight of the estolides.

According to one embodiment of the invention, typically when the method is carried out according to the route b2), the composition of estolides comprises:

from 50 to 99.8% by weight, preferentially from 55 to 90% by weight, more preferentially from 55 to 80% by weight, of monoestolides corresponding to the formula (7), and from 0.1 to 30% by weight, preferentially from 5 to 25% by weight, more preferentially from 10 to 25% by weight, of polyestolides described by the formula (8), preferentially wherein n is equal to 1, from 0.1 to 30% by weight, preferentially from 1 to 25% by weight, more preferentially from 5 to 25% by weight, of esters chosen from esters described by the formula (5) and esters described by the formula (3), with respect to the total weight of the composition of estolides.

According to one embodiment of the invention, typically when the method is carried out according to the route b1), the composition of estolides comprises:

from 55 to 99.9% by weight, preferentially from 60 to 95% by weight, more preferentially from 65 to 90% by weight, of monoestolides with the formula (7), and from 0.1 to 45% by weight, preferentially from 5 to 40% by weight, more preferentially from 10 to 35% by weight, of polyestolides with the formula (8), with respect to the total weight of the estolides.

Uses

The method according to the invention can be used for obtaining a composition of estolides exhibiting a high selectivity in favor of monoestolide. The composition of estolides according to the invention can thus be used as a base oil in a lubricating composition. The composition of estolides can be used in a lubricating composition, without a prior distillation step separating the monoestolides from the polyestolides, following the addition reaction defined in the method according to the invention.

The composition of estolides can be used in a lubricating composition as the sole base oil, but advantageously in combination with another base oil. "Other base oil" should be understood as a base oil different from the estolides.

The lubricating composition comprising the composition of estolides according to the invention can be used for lubricating the different parts of a vehicle, in particular the different parts of an engine or of a vehicle transmission or the different parts of a marine engine or of an engine for an industrial machine, e.g. for public works.

The composition of estolides which can be obtained can further be used as an emollient of a cosmetic or pharmaceutical composition, alone or in combination with another fatty substance. "Other fatty substance" should be understood as a fatty substance different from the estolides according to the invention.

The cosmetic or pharmaceutical composition comprising the composition of estolides according to the invention can be used for topical application, typically to the skin, nails, lips, hair and scalp.

The further subject matter of the invention is the cosmetic or pharmaceutical use of the composition of estolides according to the invention as a skin care product (serums, creams, balms, etc.) as a hygiene product, as a suncare/after-sun product, as a make-up product, as a make-up-removing product, as a perfumed product, as an antiperspirant product.

The invention further relates to a cosmetic or pharmaceutical method for treating the skin, nails, lips, hair or scalp, comprising at least one step of applying a composition of estolides according to the invention to the skin, nails, lips, hair or scalp.

Finally, the invention further covers a cosmetic treatment method comprising at least one step of applying, preferentially by spreading, the composition of estolides according to the invention to the skin, the nails, the lips, the hair or the scalp.

Lubricating Composition

The invention further relates to a lubricating composition comprising the composition of estolide esters according to the invention and at least one additive and/or at least one other base oil.

These other base oils can be chosen from base oils conventionally used in the field of lubricating oils, such as mineral oils, either synthetic or natural, animal or vegetable oils or mixtures thereof.

The other base oils used in the lubricating compositions according to the invention can be oils of mineral or synthetic origin belonging to groups I to V according to the classes defined by the API classification (or the equivalents thereof according to the ATIEL classification) and shown in Table 1 hereinafter or the mixtures thereof.

TABLE 1

| | Concentration of saturated substances (by weight) | Sulfur concentration (by weight) | Viscosity index (VI) |
|---|---|---|---|
| Group I Mineral oils | <90% | >0.03% | 80 ≤ VI < 120 |
| Group II Hydrocracked oils | ≥90% | ≤0.03% | 80 ≤ VI < 120 |
| Group III Hydro-isomerized or hydro-cracked oils | ≥90% | ≤0.03% | ≥120 |
| Group IV | Polyalphaolefines (PAO) | | |
| Group V | Esters and other bases not included in groups I to IV | | |

The other mineral base oils include any type of base oil obtained by atmospheric distillation and vacuum distillation of crude oil, followed by refining operations such as solvent extraction, deasphalting, solvent dewaxing, hydrotreatment, hydrocracking, hydroisomerization and hydrofinishing.

Mixtures of synthetic and mineral oils which can be bio-sourced, can further be used.

The other base oils of the lubricating compositions according to the invention can be further chosen from synthetic oils, such as certain carboxylic acid esters and alcohol esters, polyalphaolefins (PAO), and polyalkylene glycol (PAG) obtained by polymerization or copolymerization of alkylene oxides comprising from 2 to 8 carbon atoms, in particular from 2 to 4 carbon atoms.

The PAOs used as other base oils are, e.g., obtained from monomers comprising from 4 to 32 carbon atoms, e.g. from octene or decene. The weight-average molecular weight of the PAO can vary quite significantly. Preferentially, the weight-average molecular weight of the PAO is less than 600 Da. The weight-average molecular weight of the PAO can further range from 100 to 600 Da, from 150 to 600 Da, or further from 200 to 600 Da. Advantageously, when low viscosity applications are targeted, PAO 2 and/or PAO 4 will typically be chosen.

Advantageously, the other base oil or oils of the lubricating composition according to the invention are chosen from polyalphaolefins (PAO), polyalkylene glycol (PAG) and carboxylic acid esters and alcohol esters.

According to an alternative embodiment, the other base oil or oils of the lubricating composition according to the invention can be chosen from the base oils of group II or III. A person skilled in the art has to adjust the content of base oil to be used in a lubricating composition.

According to one embodiment, the lubricating composition according to the invention comprises:
 from 5 to 95% by weight, preferentially from 10 to 70% by weight, advantageously from 15 to 50% by weight, of the composition of estolide esters according to the invention, and
 from 5 to 95% by weight, preferentially from 30 to 90% by weight, advantageously from 50 to 85% by weight, of one or a plurality of other base oils,
 with respect to the total weight of the lubricating composition according to the invention.

According to one embodiment, the additive(s) of the lubricating composition are chosen from friction modifiers, detergents, anti-wear additives, extreme pressure additives, dispersants, antioxidants, pour point depressants, defoamers, metal passivators, and mixtures thereof. Such additives are well known to a person skilled in the art in the field of the lubrication of mechanical parts.

Such additives can be introduced separately and/or as a mixture similar to the additives already available for sale for commercial lubricant formulations for vehicle engines, with a performance level as defined by ACEA (European Automobile Manufacturers Association) and/or API (American Petroleum Institute), well known to a person skilled in the art.

A lubricating composition according to the invention can further comprise at least one friction modifying additive. The friction modifying additives can be chosen from compounds providing metallic elements and ashless compounds. Compounds providing metal elements include complexes of transition metals such as Mo, SB, Sn, Fe, Cu, Zn the ligands of which can be hydrocarbon compounds comprising oxygen, nitrogen, sulfur or phosphorus atoms. Ashless friction modifying additives are generally of organic origin and can be chosen from fatty acid and polyol monoesters, alkoxylated amines, alkoxylated fatty amines, fatty epoxides, fatty epoxide borates; fatty amines acid or fatty acid glycerol esters. According to the invention, fatty compounds comprise at least one hydrocarbon group comprising from 10 to 24 carbon atoms.

A lubricating composition according to the invention can comprise from 0.01 to 2% by weight or from 0.01 to 5% by weight, preferentially from 0.1 to 1.5% by weight or from 0.1 to 2% by weight of friction modifying additive, with respect to the total weight of the lubricating composition.

A lubricating composition according to the invention can comprise at least one antioxidant additive.

The antioxidant additive generally makes it possible to delay the degradation of the composition in service. Such degradation most often shows as a deposit formation, in the presence of sludge or in an increase in the viscosity of the composition.

Antioxidant additives in particular act as radical inhibitors or destroyers of hydroperoxides. The antioxidant additives commonly used include phenolic antioxidants, amine antioxidant additives, phosphosulfur antioxidant additives. Some of such antioxidant additives, e.g. phosphosulfur antioxidant additives, can generate ashes. The phenolic antioxidant additives can be ashless or in the form of neutral or basic metal salts. The antioxidant additives can in particular be chosen from sterically hindered phenols, sterically hindered phenol esters and sterically hindered phenols comprising a thioether bridge, diphenylamines, diphenylamines substituted with at least one C1-C12 alkyl group, N,N'-dialkyl-aryl-diamines and mixtures thereof.

Preferentially, according to the invention, the sterically hindered phenols are chosen from compounds comprising a phenol group of which at least one of the neighboring carbon to the carbon atom bearing the alcohol function is substituted by at least one C1-C10 alkyl group, preferentially a C1-C6 alkyl group, preferentially a C4 alkyl group, preferentially a tert-butyl group.

Amine compounds are another class of antioxidant additives which can be used, if appropriate, in combination with phenolic antioxidant additives. Examples of amine compounds are aromatic amines, e.g. aromatic amines with the formula NQ1Q2Q3 wherein Q1 represents an aliphatic group or a possibly substituted aromatic group, Q2 represents a possibly substituted aromatic group, Q3 represents a hydrogen atom, an alkyl group, an aryl group or a group of the formula Q4S(O) ZQ5 Q4 wherein Q4 represents an alkylene or alkenylene group, Q5 represents an alkyl group, alkenyl group or an aryl group and z stands for 0, 1 or 2.

Sulfur alkyl phenols or the alkali or alkaline-earth metal salts thereof can be further used as antioxidant additives.

Another class of antioxidant additives is the class of copper compounds, e.g. copper thio- or dithio-phosphate, copper salts and carboxylic acid salts, copper dithiocarbamates, copper sulfonates, copper phenates, copper acetylacetonates. Copper salts I and II, succinic acid salts or succinic anhydride salts can be used as well.

A lubricating composition according to the invention can further comprise any type of antioxidant known to a person skilled in the art.

Advantageously, the lubricating composition according to the invention comprises at least one antioxidant ashless additive.

A lubricating composition according to the invention can comprise 0.5 to 2% by weight of at least one antioxidant additive, with respect to the total weight of the composition.

A lubricating composition according to the invention can further comprise at least one detergent additive.

Detergent additives generally reduce the formation of deposits on the surface of metal parts, by dissolving oxidation and combustion by-products.

The detergent additives which can be used in the lubricating compositions according to the invention are generally known to a person skilled in the art. The detergent additives can be anionic compounds comprising a long lipophilic hydrocarbon chain and a hydrophilic head. The associated cation can be a metal cation of an alkali or alkaline earth metal.

The detergent additives are preferentially chosen from alkali metal salts or alkaline-earth metal salts of carboxylic acid, sulphonates, salicylates, naphthenates, as well as phenate salts. The alkali metals and alkaline earth metals are preferentially calcium, magnesium, sodium or barium.

Such metal salts generally include the metal in a stoichiometric amount or in an excess amount, i.e. in a concentration greater than the stoichiometric amount. Same are then overbased detergents; the metal in excess which gives the overbased character to the detergent additive is generally in the form of an oil-insoluble metal salt, e.g. a carbonate, a hydroxide, an oxalate, an acetate, a glutamate, preferentially a carbonate.

A lubricating composition according to the invention can comprise from 2 to 4% by weight of detergent additive, with respect to the total weight of the composition.

In the same way, a lubricating composition according to the invention can comprise at least one dispersing agent, distinct from the succinimide compounds defined according to the invention.

The dispersing agent can be chosen from Mannich bases, succinimides, e.g. polyisobutylene succinimides.

A lubricating composition used according to the invention can comprise e.g. from 0.2 to 10% by weight of dispersing agent(s) distinct from the succinimide type compounds defined according to the invention, with respect to the total weight of the composition.

A lubricating composition according to the invention can also comprise at least one anti-wear and/or extreme pressure agent.

There is a wide variety of anti-wear additives. Preferentially, for the lubricating composition according to the invention, the anti-wear additives are chosen from organophosphates. Same have the advantage of not forming ash and being thermally stable. Phospho-sulfur additives such as metal alkylthiophosphates, in particular zinc alkylthiophosphates, and more specifically zinc dialkyldithiophosphates or ZnDTP can be e.g. mentioned. Preferred compounds have the formula $Zn((SP(S)(OQ6)(OQ7))2$, wherein Q6 and Q7—either identical or different—independently stand for an alkyl group, preferentially an alkyl group comprising from 1 to 18 carbon atoms.

Amine phosphates as well are anti-wear and extreme pressure additives which can be used in the lubricating compositions according to the invention. However, the phosphorus provided by such additives can act as a poison in the catalytic systems of cars since same generate ash. Such effects can be minimized by partially substituting the amine phosphates with additives which do not deliver phosphorous, such as effect polysulfides, in particular sulfur-containing olefins.

A lubricating composition according to the invention can comprise from 0.01 to 15%, preferentially 0.1 to 10% by weight, preferentially 1 to 5% by weight of anti-wear agent(s), with respect to the total weight of the composition.

A lubricating composition according to the invention can further comprise at least one anti-foam additive.

The anti-foam additive can be chosen from polyacrylates, polysiloxanes or the hybrids thereof.

A lubricating composition according to the invention can comprise from 0.01 to 2% by weight or from 0.01 to 5% by weight, preferentially from 0.1 to 1.5% by weight or from 0.1 to 2% by weight of anti-foam additive, with respect to the total weight of the composition.

A lubricating composition suitable for the invention can further comprise at least one pour point depressant additive (also known as PPD agents).

By slowing down the formation of paraffin crystals, the pour point depressant additive generally improves the behavior of the composition under cold conditions. Examples of pour point depressant additives include alkyl polymethacrylates, polyacrylates, polyarylamides, polyalkylphenols, polyalkylnaphthalene, alkyls polystyrenes.

The lubricating composition according to the invention can comprise:
- from 5 to 94.9% by weight, preferentially from 10 to 70% by weight, advantageously from 15 to 50% by weight, of the composition of estolide esters according to the invention, and
- from 5 to 94.9% by weight, preferentially from 30 to 90% by weight, advantageously from 50 to 85% by weight, of one or a plurality of other base oils,
- from 0.1 to 15% by weight, preferentially from 0.5 to 10% by weight, advantageously from 1 to 5% by weight of one or a plurality of additives chosen from friction modifiers, viscosity index modifiers, detergents, dispersants, anti-wear and/or extreme pressure additives, antioxidants, pour point depressants, anti-foam additive and mixtures thereof, with respect to the total weight of the lubricating composition according to the invention.

The lubricating composition according to the invention can be obtained by mixing the constituents of the lubricating composition. The present invention further relates to the preparation method a for a lubricating composition comprising the following steps:
- preparing a composition of estolide esters according to the method described above, and
- mixing at least one other base oil and/or at least one additive with the composition of estolides.

Preferentially, the method of preparing a lubricating composition according to the invention does not comprise any intermediate step for separating the products formed during the step of preparing the composition of estolides, before the mixing step. Preferentially, the method for preparing a lubricating composition according to the invention does not comprise a hydrogenation step, in particular of hydrogenation of the composition of estolide esters obtained at the completion of the step of preparing the composition of estolides.

The other base oil(s) and the additive(s) used in the method of preparing the lubricating composition can have one or a plurality of the features described above within the framework of the lubricating composition according to the invention.

The lubricating composition obtained by this preparation method can have one or a plurality of the features described above in the context of the lubricating composition according to the invention.

Cosmetic or Pharmaceutical Composition

The further subject matter of the invention is a cosmetic or pharmaceutical composition comprising (I) the composition of estolides according to the invention and (ii) at least one fatty substance and/or (iii) at least one cosmetic additive.

Preferentially, the composition of estolides used in the cosmetic or pharmaceutical composition has one or a plurality of the features defined above within the framework of the composition of estolides.

The fatty substance can be chosen from hydrocarbon oils of biological or petrochemical origin, vegetable oils, vegetable butters, fatty ethers and alcohols, oily esters (different from the estolides according to the invention), alkanes and silicone oils.

Hydrocarbon oils are fatty substances coming from petrochemical methods. Mineral oils, isoparaffins, waxes, paraffins, polyisobutenes or polydecenes can be cited as examples.

Examples of vegetable oils include oils of wheat germ, sunflower seed, grape seed, sesame, corn, apricot, castor oils, shea and avocado oils, olive oil, soy oil, sweet almond oil, palm, rapeseed, oils of cotton, hazelnut, macadamia, jojoba, alfalfa, poppy, pumpkin, sesame, squash, rapeseed, blackcurrant, evening primrose, millet, barley, quinoa, rye, safflower, banana, passionflower, muscat rose or camellia. Vegetable butters are fatty substances which have the same properties as vegetable oils. The difference between the two consists of the fact that butters are in solid form at room temperature. Also, unlike vegetable oils, the raw material from which a butter is extracted (pulp, seeds or almonds) is heated after being ground for the extraction of the fat. Like vegetable oils, butters can be refined to ensure better preservation, neutralize odors, improve color and consistency. Rich in antioxidants and nourishing, the cosmetic properties of vegetable butters improve the elasticity of the skin, protect against external aggressions by leaving a protective film on the epidermis, thus reducing dehydration, repair and butters soothe by regenerating the natural hydrolipidic film of the skin. Examples of vegetable butters include shea butter, cocoa butter, mango butter, shorea butter and olive butter.

Ethers and fatty alcohols are long-chain fatty waxy substances with remarkable properties such as film-forming, emollient, moisturizing, softening and protective properties. They act as moisturizing oils and emulsifiers. Examples of fatty alcohol or ethers are: cetyl alcohol, Stearyl alcohol, myristyl alcohol, auryl alcohol, behenyl alcohol, Cetearyl alcohol, dicaprylyl ethers, stearyl ethers or octyldodecanol (identified by their INCI name).

The oily esters or esterified oils (distinct from the esterolides of the invention) are the product of a reaction between fatty acids (acids with longer chains, such as e.g. stearic acid, oleic acid, palmitic acid) and alcohols (fatty alcohols or polyols such as glycerol). These oils can contain substances derived from petrochemicals, as is the case for isopropyl palmitate. Examples of oily esters are caprylic capric triglyceride, coco caprylate caprate, oleyl erucate, oleyl linoleate, decyl oleate or PPG-3 benzyl ether myristate (identified by their INCI name).

Silicone or polysiloxane oils are understood to mean an oil comprising at least one silicon atom, and in particular at least one Si—O group. As silicone oil, mention can be made in particular of phenylpropyldimethylsiloxysilicate, dimethicones or cyclopentasiloxane (identified by their INCI name).

The additive, distinct from the fatty substance and from the composition of estolides, can be chosen from any adjuvant or additive usually used in the fields considered and in particular in the cosmetic, dermatological or pharmaceutical fields. A person skilled in the art will take care to select the optional additive(s) of the composition according to the invention such that the advantageous properties, intrinsically associated with the emollient composition in accordance with the invention, are not or not substantially adversely affected by the envisaged addition. Among the conventional adjuvants which can be comprised therein (depending on the water-soluble or liposoluble nature of these adjuvants), mention can be made in particular of anionic foaming surfactants (such as sodium lauryl ether sulfate, sodium alkyl phosphate, sodium trideceth sulfate), amphoteric foaming surfactants (such as alkyl betaine, disodium coamphodiacetate) Or nonionic with an HLB greater than 10 (such as POE/PPG/POE, alkylpolyglucoside, polyglyceryl-3-hydroxylauryl ether); preservatives; sequestering agents (EDTA); antioxidants; fragrances; coloring materials such as soluble dyes, pigments and nacres; matting, firming, whitening or exfoliating fillers; hydrophilic or lipophilic cosmetic active agents having the effect of improving the cosmetic properties of the skin, electrolytes; hydrophilic or lipophilic, anionic, nonionic, cationic or amphoteric polymers, thickeners, gelling or dispersing agents; slimming agents such as caffeine; optical brighteners; antisebohrreic compounds; and their mixture. The amounts of these various cosmetic adjuvants are those conventionally used in the field under consideration, and e.g. the cosmetic composition comprises an overall content ranging from 0.01 to 20% by weight of additives with respect to the total weight of the composition.

In the case where the cosmetic, dermatological or pharmaceutical composition of the invention is a dermatological or pharmaceutical composition, said composition can comprise one or a plurality of therapeutic active ingredients. As active ingredients which can be used in the dermatological or pharmaceutical composition of the invention, mention can be made, e.g., of sunscreens; Water-soluble or fat-soluble vitamins such as vitamin A (retinol), vitamin E (tocopherol), vitamin C (ascorbic acid), vitamin B5 (panthenol), vitamin B3 (niacinamide), derivatives of these vitamins (especially esters) and mixtures thereof; antiseptics; antibacterial active agents such as 2,4,4'-trichloro-2'-hydroxydi phenyl ether (or triclosan), 3,4,4'-trichlorocarbanilide (or triclocarban); antimicrobials such as benzoyl peroxide, niacin (vitamin PP); and mixtures thereof.

This cosmetic or pharmaceutical composition comprises a physiologically acceptable medium, that is to say one which does not have deleterious side effects and in particular which does not produce redness, heating, tightness or stinging which is unacceptable to a user.

According to one embodiment, the cosmetic, dermatological or pharmaceutical composition has a content of the composition of estolides according to the invention ranging from 0.5 to 80%, preferentially from 1 to 50% and advantageously from 5 to 30% by weight with respect to the total weight of the cosmetic or pharmaceutical composition.

According to one embodiment of the invention, the cosmetic or pharmaceutical composition comprises, with respect to the total weight of the cosmetic or pharmaceutical:
    from 0.5 to 80% by weight, preferentially from 1 to 50% by weight and advantageously from 5 to 30% by weight, of the composition of estolides according to the invention,
    from 0 to 90% by weight, preferentially from 5 to 80% by weight and advantageously from 10 to 70% by weight, preferentially from 20 to 60% by weight and advantageously from 30 to 50% by weight, of fatty substances,
    0 to 20% by weight of additives,
    0 to 20% by weight of therapeutic active ingredients,
    it should be understood that the composition comprises at least one additive or at least one fatty substance.

According to one embodiment of the invention, the cosmetic or pharmaceutical composition comprises, with respect to the total weight of the cosmetic or pharmaceutical:
    from 0.5 to 80% by weight, preferentially from 1 to 50% by weight and advantageously from 5 to 30% by weight, of the composition of estolides according to the invention,
    From 0 to 90% by weight, preferentially from 5 to 80% by weight and advantageously from 10 to 70% by weight, preferentially from 20 to 60% by weight and advantageously from 30 to 50% by weight, of fatty substances chosen from hydrocarbon oils of biological or petrochemical origin, vegetable oils, vegetable butters, fatty ethers and alcohols, oily esters (other than estolides), alkanes and silicone oils, 0 to 20% by weight of additives chosen from anionic, amphoteric or nonionic foaming surfactants with HLB greater than 10; preservatives; sequestering agents; antioxidants; perfumes; Coloring materials; mattifying, firming bleaching or exfoliating fillers; hydrophilic or lipophilic cosmetic active ingredients comprising the effect of improving the cosmetic properties of the skin, electrolytes; hydrophilic or lipophilic, anionic, nonionic, cationic or amphoteric, thickening polymers; gelling or dispersing agents; slimming agents; optical brighteners; antisebohrreic compounds; and mixtures thereof, optionally from 0 to 20% by weight of therapeutic active ingredients, it should be understood that the composition comprises at least one additive or at least one fatty substance.

The cosmetic or pharmaceutical composition according to the invention can thus be an anhydrous composition, an emulsion such as a water-in-oil (W/O) emulsion, an oil-in-water (O/W) emulsion or a multiple emulsion (in particular W/O/W or O/W/O), a nano-emulsion, or alternatively a dispersion.

The cosmetic or pharmaceutical composition according to the invention is in the form of a more or less soft cream or of a vaporizable emulsion. It can comprise, e.g., a composition for removing make-up or cleansing the skin, the lips, an after-sun composition, a composition for massaging the skin, a shower balm composition, an antiperspirant composition, a mask composition, a restorative balm composition, a scrub and/or exfoliating composition for both the face and the hands (when it contains exfoliating particles), a make-up composition, a shaving composition, an after-shave balm composition, a perfumed composition, a composition for wipes or a vaporizable composition.

The cosmetic or pharmaceutical composition according to the invention can also comprise a sunscreen composition when it includes at least one sunscreen.

The cosmetic or pharmaceutical composition according to the invention is a cosmetic composition when it provides only a cosmetic effect. Typically, the cosmetic composition according to the invention is free of therapeutic active agents.

On the other hand, the cosmetic or pharmaceutical composition according to the invention is a dermatological or pharmaceutical composition when it provides a therapeutic effect. Typically, the dermatological or pharmaceutical composition according to the invention comprises at least one therapeutic active agent, e.g. chosen from sunscreens; antiseptics; antibacterial active agents such as 2,4,4'-trichloro-2'-hydroxydiphenyl ether (or triclosan), 3,4,4'-trichlorocarbanilide (or triclocarban); antimicrobials such as benzoyl peroxide, niacin (vitamin PP); and mixtures thereof.

EXAMPLES

In the remainder of the present description, examples are given by way of illustration of the present invention and under no circumstances are intended to limit its scope.

The conversion corresponds to the proportion by weight of the starting hydroxycarboxylic acid compound which has reacted.

The monoestolide selectivity corresponds to the proportion by weight of monoestolides obtained in the composition of estolides obtained from the method.

In the remainder of the examples, the following products were used:
12-HSA=12-hydroxystearic acid,
C9=nonanoic acid,
2EOH=2-ethylhexanol,
tin oxalate=catalyst
FASCAT® 4100=tin catalyst with CAS number 2273-43-0.

Example 1: Implementation of the Method by Adding Fatty Acid and then Adding Alcohol Two protocols were implemented according to this route, depending on the mode of introduction of the hydroxycarboxylic acid.

Protocol 1: Continuous addition of hydroxycarboxylic acid to the saturated acid

Nonanoic acid and the catalyst are introduced into a 500 mL three-necked flask equipped with a magnetized bar, said flask being equipped with a condenser, a nitrogen bubbler and a Dean Stark. The reaction medium is heated under a stream of nitrogen to 190° C. and then, using a powder dispensing funnel, the 12-hydroxystearic acid is introduced in small portions over 3 hours.

The progress of the reaction is monitored by GPC. After reacting for 8 hours, the excess nonanoic acid is distilled under vacuum (2.5 mbar at 200° C.). The acid estolide thus obtained is then esterified (without removing the catalyst) with 2-ethylhexanol in the presence of a catalyst. The evolution of the esterification is monitored by measuring the acid number and the formation of the ester band by infrared. The excess of 2-ethylhexanol is removed by distillation under reduced pressure (200° C., 2.5 mbar). At the completion of the distillation, the reaction medium is allowed to cool to 100° C. and then filtered on filter paper of porosity 0.7 µm. The estolide thus obtained is in the form of a yellowish oil.

Protocol 2: addition of "one pot" of hydroxycarboxylic acid and saturated acid

Nonanoic acid, 12-hydroxystearic acid and the catalyst are introduced into a 500 mL three-necked flask equipped with a magnetized bar, said flask being equipped with a condenser, a nitrogen bubbler and a Dean Stark. The reaction medium is heated under a stream of nitrogen to 190° C. The progress of the reaction is monitored by GPC. After reacting for 8 hours, the excess nonanoic acid is distilled under vacuum (2.5 mbar at 200° C.). The acid estolide thus obtained is then esterified (without removing the catalyst) with 2-ethylhexanol in the presence of a catalyst. The evolution of the esterification is monitored by measuring the acid number and the formation of the ester band by infrared. The excess of 2-ethylhexanol is removed by distillation under reduced pressure (200° C., 2.5 mbar). At the completion of the distillation, the reaction medium is allowed to cool to 100° C. and then filtered on filter paper of porosity 0.7 µm. The estolide thus obtained is in the form of a yellowish oil.

The acid estolide formed at the completion of the first reaction corresponds to the formula (10) and the estolide ester formed at the completion of the second reaction corresponds to the formula (11).

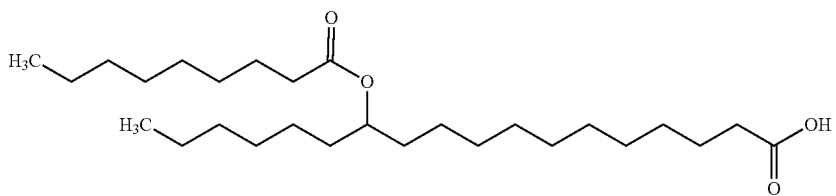

[Chem 10]

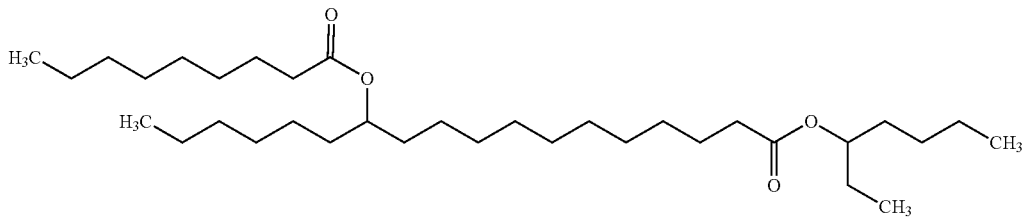

[Chem 11]

The conditions for the first reaction (in this example, reaction of addition of a fatty acid to the alcohol function of the hydroxycarboxylic acid) are given in Table 2 below. Conversion and selectivity are also indicated.

TABLE 2

| | Protocol | Catalyst (cata) | Molar ratio 12-HSA/C9 | % by mass of cata with respect to the total weight (12-HSA + C9 + cata) | Conversion (%) | Selectivity (%) |
|---|---|---|---|---|---|---|
| Ex1 | 1 | Fascat ® 4100 | 1/3 | 0.025% | 92.1 | 66.5 |
| Ex2 | 1 | Tin oxalate | 1/3 | 0.025% | 93.7 | 66.5 |
| Ex3 | 1 | Tin oxalate | 1/2 | 0.025% | 90.4 | 53.5 |
| Ex4 | 2 | Tin oxalate | 1/3 | 0.025% | 93.8 | 58.8 |
| ExC1 | 1 | Tin oxalate | 1/1 | 0.025% | 95.0 | 33.9 |

The conditions for the second reaction (in this example, reaction for esterification of the acid function of the acid estolide obtained from the first reaction) are given in Table 3 below. Conversion and selectivity are also indicated.

TABLE 3

| | Protocol | Catalyst (cata) | Molar ratio Acid estolide/2EOH | Weight % of cata with respect to the total weight (acid estolide + 2EOH + cata) | Conversion (%) | Selectivity (%) |
|---|---|---|---|---|---|---|
| Ex1 | 1 | Fascat ® 4100 | 1/1.4 | 0.025% | 85.1 | 67.9 |
| Ex2 | 1 | Tin oxalate | 1/1.4 | 0.025% | 83.4 | 68.0 |
| Ex3 | 1 | Tin oxalate | 1/1.4 | 0.025% | 87.0 | 54.0 |
| Ex4 | 2 | Tin oxalate | 1/1.4 | 0.025% | 89.0 | 61.0 |
| ExC1 | 1 | Tin oxalate | 1/1.4 | 0.025% | 87.2 | 37.9 |

The results of this table show a very good conversion and a good selectivity to monoestolide for the examples according to the invention Ex1 to Ex4.

It was found that the selectivity was significantly less good for the example ExC1 used with a ratio of 1/1 hydroxycarboxylic acid and fatty acid.

The composition of estolides Ex1 to Ex4 and the composition ExC1 were evaluated in terms of kinematic viscosity, pour point and acid number.

The following methods were used:

The kinematic viscosities at 40° C. (KV40) and at 100° C. (KV100) were determined according to the ASTM D445 standard.

The pour point (PE) was determined according to ASTM D7346 or ASTM D97.

The acid number was determined according to ASTM D974 standards.

The results are shown in the Table 4 below. Table 4 also shows the amounts of monoestolides and the amounts of polyestolides, with respect to the total weight of the composition of estolides.

TABLE 4

| | Weight % of monoestolides | weight % of polyestolides | KV40 (CST) | KV100 (CST) | PE (° C.) | acid number (mgKOH/g) |
|---|---|---|---|---|---|---|
| Ex1 | 66.51 | 33.49 | 23.25 | 5.31 | −21 | 0.26 |
| Ex2 | 66.50 | 33.50 | 29.19 | 6.09 | −18 | 0.14 |
| Ex3 | 53.54 | 46.46 | 36.42 | 7.21 | −15 | 1.8 |
| Ex4 | 58.84 | 41.16 | 31.94 | 6.58 | −24 | 0.08 |
| ExC1 | 33.93 | 66.07 | 39.61 | 7.75 | −18 | 1.05 |

The characteristics of Table 4 show that the composition of estolides according to the invention have good properties, allowing them to be used as a base oil in lubricating compositions.

Example 2: Implementation of the Method by Adding Alcohol Followed by Adding a Fatty Acid The following protocol was used: Continuous addition of hydroxycarboxylic acid to the alcohol 2-ethylhexanol and the catalyst are introduced into a 500 ml three-necked flask equipped with a magnetized bar, said flask being equipped with a condenser, a nitrogen bubbler and a Dean Stark. The reaction medium is heated under a stream of nitrogen to 190° C. and then, using a powder dispensing funnel, the 12-hydroxystearic acid is introduced in small portions over 3 hours. The progress of the reaction is monitored by measuring the variation in the acid number in the reaction medium. After reacting for 12 hours, the excess 2-ethylhexanol is distilled under vacuum (2.5 mbar at 200° C.). The 2-ethylhexyl hydroxystearate thus obtained is then capped with nonanoic acid (without removing the catalyst). The evolution of esterification is monitored by GPC analysis.

The excess acid is removed by distillation under reduced pressure (200° C., 2.5 mbar). At the completion of the distillation, the reaction medium is allowed to cool to 100° C. and then filtered on filter paper of porosity 0.7 μm. The estolide thus obtained is in the form of a yellowish oil.

The conditions for the first reaction (in this example, esterification reaction with an alcohol on the acid function of the hydroxycarboxylic acid) are given in Table 5 below. Conversion and selectivity are also indicated.

TABLE 5

| | Catalyst (cata) | Molar ratio 12-HSA/ 2EOH | Weight % of cata with respect to the total weight (12-HSA + C9 + cata) | Conversion (%) | Selectivity (%) |
|---|---|---|---|---|---|
| Ex5 | Fascat® 4100 | 1/3 | 0.05% | 100.0 | 92.8 |
| Ex6 | Fascat® 4100 | 1/3 | 0.025% | 100.0 | 93.3 |

The conditions for the second reaction (in the present example, reaction for adding a saturated fatty acid to the hydroxyl function of the hydroxycarboxylic acid ester obtained from the first reaction) are given in Table 6 below. Conversion and selectivity are also indicated.

TABLE 6

| | Catalyst (cata) | Molar ratio 12-HSA/ C9 ester | Weight % of cata, with respect to the total weight (ester of 12-HSA + C9 + cata) | Conversion (%) | Selectivity (%) |
|---|---|---|---|---|---|
| Ex5 | Fascat® 4100 | 1/1.4 | 0.05% | 94.4 | 64.9 |
| Ex6 | Fascat® 4100 | 1/1.4 | 0.025% | 90.0 | 77.7 |

The results of this table show a very good conversion and a selectivity which increases when the quantity of catalyst is reduced.

The compositions of Ex5 and Ex6 estolides were evaluated in terms of kinematic viscosity and pour point.

The following methods were used:
  The kinematic viscosities at 40° C. (KV40) and at 100° C. (KV100) were determined according to the ASTM D445 standard.
  The pour point (PE) was determined according to ASTM D7346 or ASTM D97.

The results are shown in the Table 7 below. Table 7 also shows the amounts of monoestolides and the amounts of polyestolides, with respect to the total weight of the composition of estolides.

TABLE 7

| | Weight % of monoestolides | weight % of polyestolides | KV40 (CST) | KV100 (CST) | PE (° C.) |
|---|---|---|---|---|---|
| Ex5 | 64.94 | 35.06 | 35.23 | 7.04 | −24 |
| Ex6 | 77.7 | 22.3 | 26.81 | 5.83 | −21 |

The characteristics of Table 7 show that the composition of estolides according to the invention have good properties, allowing them to be used as a base oil in lubricating compositions.

We claim:

1. A method for preparing a composition C5 of estolide esters, said method comprising:
    a) providing a composition C1 comprising at least one hydroxycarboxylic acid containing from 10 to 30 carbon atoms,
    (b) followed by:
        b1) the introduction of a composition C2 comprising at least one saturated acid containing 2 to 18 carbon atoms, into the composition C1 in order to obtain a composition C3 of acid estolides, the hydroxycarboxylic acid/saturated fatty acid molar ratio being from 1/2 to 1/8, followed by the introduction of a composition C4 comprising at least one saturated alcohol containing 1 to 16 carbon atoms, into the composition C3, or b2) the introduction of a composition C4 comprising at least one saturated alcohol containing 1 to 16 carbon atoms, into composition C1 in order to obtain a composition C6 of hydroxycarboxylic acid ester, followed by the introduction of a composition C2 comprising at least one saturated acid containing from 2 to 18 carbon atoms, into the composition C6, the molar ratio of hydroxycarboxylic acid ester to saturated fatty acid is from 1/1.4 to 1/6 when the method is carried out according to route b2), (c) obtaining a composition C5 of estolide esters, wherein said at least one hydroxycarboxylic acid is a saturated acid.

2. The method according to claim 1, wherein the hydroxycarboxylic acid has the formula [Chem 1], the saturated fatty acid has the formula [Chem 2] and the saturated alcohol has the formula [Chem 4]:

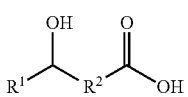

[Chem 1]

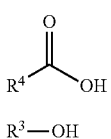

[Chem 2]

R³—OH

[Chem 4]

wherein:
R¹ represents a linear or branched alkyl radical comprising from 1 to 27 carbon atoms,
R² represents a linear or branched divalent alkylene radical comprising from 1 to 27 carbon atoms,
where it is understood that the total number of carbon atoms of R¹ and R² ranges from 8 to 28 carbon atoms,
R³ represents a linear or branched monovalent alkyl radical containing from 1 to 16 carbon atoms,
R⁴ represents a linear or branched monovalent alkyl radical containing from 1 to 17 carbon atoms.

3. The method according to claim 1, wherein the C5 composition of estolide esters comprises monoestolides with the formula [Chem 7]:

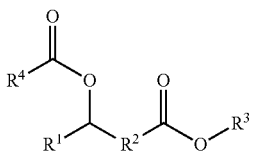

[Chem 7]

wherein R¹, R², R³ and R⁴ have the same definition as in claim 2.

4. The method according to claim 1, wherein the introduction of the composition C2 comprising at least one saturated acid containing from 2 to 18 carbon atoms leads to fatty acid addition reaction(s), and wherein the catalyst for the fatty acid addition reaction is used in an amount ranging from 0.01 to 0.1% by weight, with respect to the total weight of the reaction medium.

5. The method according to claim 1, comprising:
b1) the reaction of said saturated acid with the hydroxyl function of said hydroxycarboxylic acid at a temperature ranging from 120 to 280° C., for obtaining acid estolides, followed by the reaction of said saturated alcohol with the acid function of the acid estolides at a temperature ranging from 120 to 280° C., for obtaining a composition C5 of estolide esters, or b2) the reaction of said saturated alcohol with the acid function of the hydroxycarboxylic acid ester at a temperature ranging from 120 to 280° C., for obtaining the esters of the hydroxycarboxylic acid and of the alcohol, followed by the reaction of said saturated acid on the hydroxyl function of the esters of the hydroxycarboxylic acid and of the alcohol at a temperature ranging from 120 to 280° C., for obtaining a composition C5 of estolide esters.

6. The method according to claim 1, carried out according to the route b1).

7. A composition of estolide esters obtainable by the method according to claim 1, comprising, with respect to the total weight of the estolides:
more than 50% to 99.9% by weight of monoestolide ester(s) with the formula [Chem 7], and
from 0.1 to less than 50% by weight of the polyestolide ester(s) with the formula [Chem 8],
with

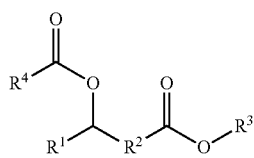

[Chem 7]

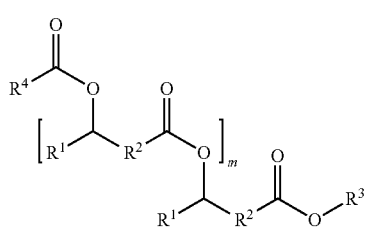

[Chem 8]

wherein:
R¹ represents a linear or branched alkyl radical comprising from 1 to 27 carbon atoms,
R² represents a linear or branched divalent alkylene radical comprising from 1 to 27 carbon atoms,
where it is understood that the total number of carbon atoms of R¹ and R² ranges from 8 to 28 carbon atoms,
R³ represents a linear or branched monovalent alkyl radical containing from 1 to 16 carbon atoms,
R⁴ represents a linear or branched monovalent alkyl radical containing from 1 to 17 carbon atoms, and
m is a number different from zero.

8. A method for preparing a cosmetic or pharmaceutical composition, the method comprising using the composition of estolide esters according to claim 7 as an emollient in the cosmetic or pharmaceutical composition.

9. A lubricating composition comprising the composition of estolide esters according to claim 7 and at least one base oil different from the estolide esters and/or at least one additive different from the estolide esters.

10. The method according to claim 1, wherein the molar ratio of hydroxycarboxylic acid to saturated fatty acid is from 1/2 to 1/6 when the method is carried out according to the route b1) and the molar ratio of hydroxycarboxylic acid ester to saturated fatty acid is from 1/1.4 to 1/4 when the method is carried out according to the route b2).

11. The method according to claim 2, wherein:
$R^1$ represents a linear or branched alkyl radical comprising from 3 to 18 carbon atoms,
$R^2$ represents a linear or branched divalent alkylene radical comprising from 4 to 22 carbon atoms,
where it is understood that the total number of carbon atoms of $R^1$ and $R^2$ ranges from 6 to 24 carbon atoms,
$R^3$ represents a linear or branched monovalent alkyl radical containing from 1 to 12 carbon atoms,
$R^4$ represents a linear or branched monovalent alkyl radical containing from 2 to 12 carbon atoms.

12. The method according to claim 2, wherein:
$R^1$ represents a linear or branched alkyl radical comprising from 5 to 12 carbon atoms,
$R^2$ represents a linear or branched divalent alkylene radical comprising from 8 to 18 carbon atoms,
where it is understood that the total number of carbon atoms of $R^1$ and $R^2$ ranges from 10 to 20 carbon atoms,
$R^3$ represents a linear or branched monovalent alkyl radical containing from 1 to 10 carbon atoms, $R^4$ represents a linear alkyl containing from 4 to 12 carbon atoms.

13. The method according to claim 1, wherein the catalyst for the fatty acid addition reaction is used in an amount ranging from 0.02 to 0.08% by weight, with respect to the total weight of the reaction medium.

14. The composition according to claim 7, wherein:
$R^1$ represents a linear or branched alkyl radical comprising from 3 to 18 carbon atoms,
$R^2$ represents a linear or branched divalent alkylene radical comprising from 4 to 22 carbon atoms,
where it is understood that the total number of carbon atoms of $R^1$ and $R^2$ ranges from 6 to 24 carbon atoms,
$R^3$ represents a linear or branched monovalent alkyl radical containing from 1 to 12 carbon atoms,
$R^4$ represents a linear or branched monovalent alkyl radical containing from 2 to 12 carbon atoms, and
m is a number different from zero.

15. The composition according to claim 7, wherein:
$R^1$ represents a linear or branched alkyl radical comprising from 5 to 12 carbon atoms,
$R^2$ represents a linear or branched divalent alkylene radical comprising from 8 to 18 carbon atoms,
where it is understood that the total number of carbon atoms of $R^1$ and $R^2$ ranges from 10 to 20 carbon atoms,
$R^3$ represents a linear or branched monovalent alkyl radical containing from 1 to 10 carbon atoms,
$R^4$ represents a linear alkyl containing from 4 to 12 carbon atoms, and m is a number ranging from 1 to 4.

* * * * *